(12) United States Patent
Heismann et al.

(10) Patent No.: US 7,212,603 B2
(45) Date of Patent: May 1, 2007

(54) DEVICE FOR CAPTURING STRUCTURAL DATA OF AN OBJECT

(75) Inventors: Björn Heismann, Erlangen (DE); Thomas Mertelmeier, Erlangen (DE)

(73) Assignee: Siemens Akitengesellschaft, Munich (DE)

( * ) Notice: Subject to any disclaimer, the term of this patent is extended or adjusted under 35 U.S.C. 154(b) by 0 days.

(21) Appl. No.: 10/920,819

(22) Filed: Aug. 18, 2004

(65) Prior Publication Data
US 2005/0041770 A1 Feb. 24, 2005

(30) Foreign Application Priority Data
Aug. 18, 2003 (DE) ................ 103 37 935

(51) Int. Cl.
G01N 23/00 (2006.01)
G21K 1/00 (2006.01)
H05G 1/00 (2006.01)
H01J 35/14 (2006.01)

(52) U.S. Cl. .............. 378/9; 378/19; 378/122; 378/145

(58) Field of Classification Search .......... 378/7, 378/154, 27, 39, 91, 113, 138, 147, 149, 174, 378/193, 203, 901, 4, 9, 11, 12, 15, 19, 122, 378/145; 250/397, 398, 370.09, 491.1, 492.22
See application file for complete search history.

(56) References Cited

U.S. PATENT DOCUMENTS

| | | | | |
|---|---|---|---|---|
| 4,093,859 A | * | 6/1978 | Davis et al. ........... 378/7 |
| 4,149,248 A | * | 4/1979 | Pavkovich ........... 378/14 |
| 4,446,521 A | * | 5/1984 | Inouye ........... 378/14 |
| 5,335,255 A | * | 8/1994 | Seppi et al. ........... 378/4 |
| 6,067,342 A | * | 5/2000 | Gordon ........... 378/19 |
| 6,125,167 A | * | 9/2000 | Morgan ........... 378/124 |
| 6,353,227 B1 | * | 3/2002 | Boxen ........... 250/363.1 |
| 6,842,502 B2 | * | 1/2005 | Jaffray et al. ........... 378/65 |

OTHER PUBLICATIONS

Wolfgang Härer, Günter Lauritsch, Thomas Mertelmeier, Karl Wiesent, "Rekonstruktive Röntgenbildgebung", Physikalische Blätter, 1999, pp. 37-42. vol. 55, No. 3, Germany.

Edward G. Solomon, Brian P. Wilfley, Michael S. Van Lysel, Aaron W. Joseph, Joseph A. Heanue, "Scanning-beam Digital X-Ray (SBDX) System for Cardiac Angiography", Feb. 1999, pp. 246-257, SPIE vol. 3659, San Diego, California.

Edward G. Solomon, Michael S. Van Lysel, Robert E. Melen, Jack W. Moorman, Brian Skillicorn, "Low-Exposure Scanning-Beam X-Ray Fluoroscopy System", SPIE, 1996, pp. 140-149, vol. 2708.

* cited by examiner

*Primary Examiner*—Edward J. Glick
*Assistant Examiner*—Anastasia S. Midkiff

(57) ABSTRACT

To simplify the reconstruction of structural data of an object (7) examined using a tomography device (1), it is proposed to implement a radiation source (4) in such a way that radiation bundles (6) with parallel beam geometry are produced.

14 Claims, 1 Drawing Sheet

DEVICE FOR CAPTURING STRUCTURAL DATA OF AN OBJECT

CROSS REFERENCE TO RELATED APPLICATIONS

This application claims priority to the German application No. 10337935.5, filed Aug. 18, 2003 and which is incorporated by reference herein in its entirety.

FIELD OF INVENTION

The invention relates to a device for capturing structural data of an object, having:
 a radiation source that can be moved around the object along a prescribed trajectory;
 a detector disposed on the opposite side of the object and which can be moved according to the movement of the radiation source, the detector having a plurality of adjacently disposed detector sections and generating projection data of the object; and
 an evaluation unit which calculates the object's structural data from the projection data acquired by the detector.

BACKGROUND OF INVENTION

Such devices are generally known as computer tomography equipment. An overview of the various devices and methods may be found in the publication HARER, Wolfgang et al., "Rekonstruktive Röntgenbildgebung" [Reconstructive X-Ray Imaging] in Phys. Bl., 1999, Volume 55, pages 37 to 42. The known devices have a point radiation source which is moved around a patient to be examined along a circular focal point trajectory or a helix. The radiation cone emitted by the virtually point radiation source passes through the patient and is incident on a large-area detector which is moved according to the movement of the X-ray source and onto which an image corresponding to the structure of the patient's inside is projected. The structural data of the patient's inside can then be at least approximately determined from the projection data captured by the detector.

SUMMARY OF INVENTION

Various methods have been developed for converting the projection data into structural data. In the case of a circular orbit of the radiation source around the object to be examined, there is an approximate solution for computing the structural data: the so-called Feldkamp algorithm. If the orbit constitutes a so-called complete focal point trajectory, e.g. a circle and a line orthogonal to the plane of the circle, two orthogonal circles or a helix, precise solutions exist. However, the algorithms used for reconstructing the structural data are complex, as the projection data is generated using a radiation cone. The known algorithms, e.g. of Grangeat, Smith, Tam, Defrise, Kudo and Katsevich, suffer from extremely long compute times, numerical instabilities and difficulties in reconstructing sub-areas of an object under examination.

Moreover, from the publication SOLOMON, E. et al., "Scanning-beam digital X-ray (SBDX) system for cardiac angiography" in Proc. SPIE Medical Imaging Conference, February 1999, and from the publication SOLOMON, E. et al., "Low-exposure scanning-beam X-ray fluoroscopy system", in Proc. SPIE, 1996, Volume 2708, pages 140–149, a device having a large-area X-ray source is known. The X-ray source comprises a vacuum tube in which an electron beam scans a transmission target in the form of a thin film. The X-rays produced in the transmission target are aligned to a detector by a so-called collimator disposed in front of the vacuum tube. The so-called collimator is a hole collimator having a total of more than 100×100 adjacent holes made from an X-ray-absorbing material. The longitudinal axes of the holes are each aligned to the detector. In addition, the holes widen out in the radiation direction to produce a plurality of conical X-rays with a small aperture angle whose solid angle in each case corresponds to the solid angle which the detector picks up from the X-ray source.

Compared to the X-ray source, the detector of the known device only has a small area and the number of pixels of the detector is correspondingly low. The detector only has 48×48 pixels.

While the electron beam is scanning the transmission target, the detector is consecutively illuminated through the individual holes of the so-called collimator from different directions with cone-shaped X-rays. Correspondingly an object located between X-ray source and detector is also transilluminated from different directions. The structural data in various layers of the object can then be determined from the projected images captured by the detector using a tomosynthesis method. However, this is an approximate solution with severely limited depth resolution, as the object under test is only scanned from a small angular range. Accordingly, although the known device can be used in fluoroscopy and cardiology, complete reconstruction of three-dimensional structural data is not possible.

Based on this prior art, an object of the invention is to create a device for capturing structural data wherein the structural data can be easily reconstructed.

This object is achieved by the claims. Advantageous embodiments and developments are set forth in dependent claims.

The device is characterized by a radiation source having a plurality of adjacently disposed emission sections each applying radiation to an assigned section of the detector. In addition, the evaluation unit is set up to determine the structural data from the projection data using an algorithm assuming parallel radiation between radiation source and detector. As the radiation source has a plurality of adjacently disposed emission sections each applying radiation to an assigned section of the detector, the cone beam with large aperture angle known from the prior art is replaced by a plurality of adjacently disposed, virtually parallel radiation bundles with no beam divergence, the term radiation bundle also being taken to mean a cone beam originating from a point.

Because of the beam geometry it is possible to convert the projection data into structural data using an algorithm based on parallel beam geometry, the errors induced by disregarding the beam divergence being generally negligible. In addition, the algorithms based on parallel beam geometry can be performed with low compute time and are little prone to numerical instabilities.

In a preferred embodiment, the reconstruction method for the structural data is based on the Fourier Slice Theorem. The reconstruction method can be performed either two-dimensionally by evaluating the projection data captured from a row of detector sections, or three-dimensionally by evaluating the projection data captured jointly from all the detector sections. The advantage of this procedure is that algorithms can be used for which stable numerical solutions exist.

In a further preferred embodiment, the radiation source is an X-ray source with an X-ray emission region and having a downstream collimator in the beam path to the detector. An arrangement of this kind enables bundles of X-rays with low beam divergence to be achieved. To suppress stray radiation, a second collimator is preferably disposed in the beam path preceding the detector.

Further features and advantages of the invention will emerge from the following description in which exemplary embodiments of the invention will be explained in detail with reference to the accompanying drawings.

DETAILED DESCRIPTION OF INVENTION

Figure 1:
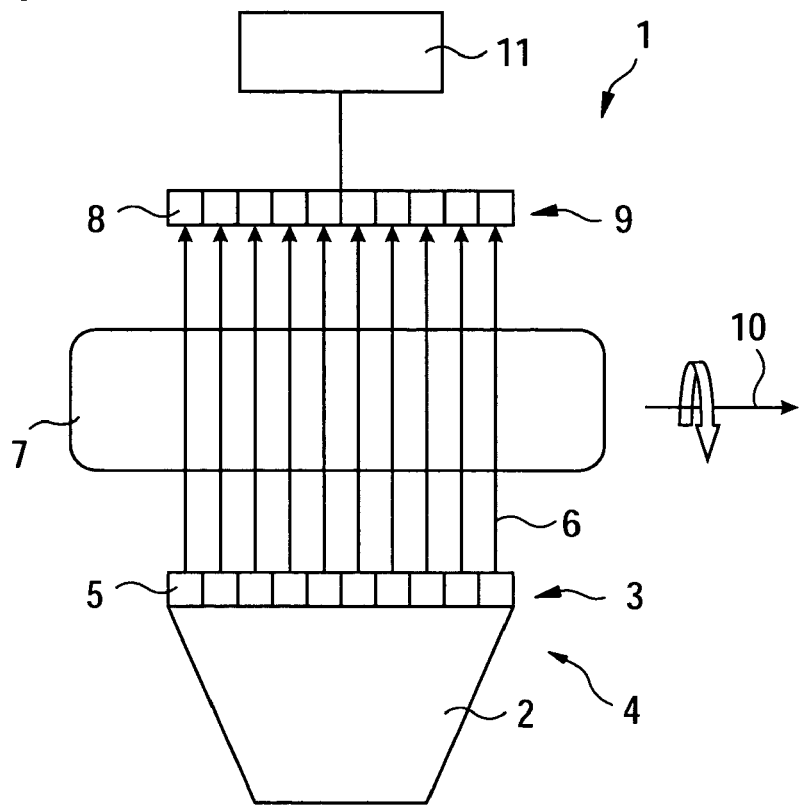
FIG. 1 shows a tomography device with parallel beam geometry.

FIG. 1 shows a tomography device 1 comprising an X-ray generator 2 with downstream collimator 3. The X-ray generator 2 and the collimator 3 constitute a radiation source 4 having a plurality of adjacently disposed emission sections 5 from which parallel aligned radiation bundles 6 are emitted. The radiation bundles 6 penetrate an object 7 which can be a patient, for example, and are incident on assigned sections 8 of a detector 9 connected to an evaluation unit 11. The number of detector sections 8 is therefore equal to the number of emission sections 5.

The collimator 3 causes the individual radiation bundles 6 to be aligned essentially parallel with minimal beam divergence. Correspondingly, each detector section 8 essentially only receives radiation from an opposite emission section 5. In particular more than 75%, preferably more than 80% or even more than 95% of the power of the radiation bundles 6 emitted from the emission sections 5 is incident on the relevant assigned detector section 8.

Through the partial absorption of the radiation bundles 6 in the object 7, the detector 9 captures a shadow projection of the internal structure of the object 7. If the radiation source 4 and the detector 9 are revolved about a rotational axis 10 around the object 7 while projection data is repeatedly captured, structural data describing the internal structure of the object 7 under test can be computed from the projection data.

Figure 2:
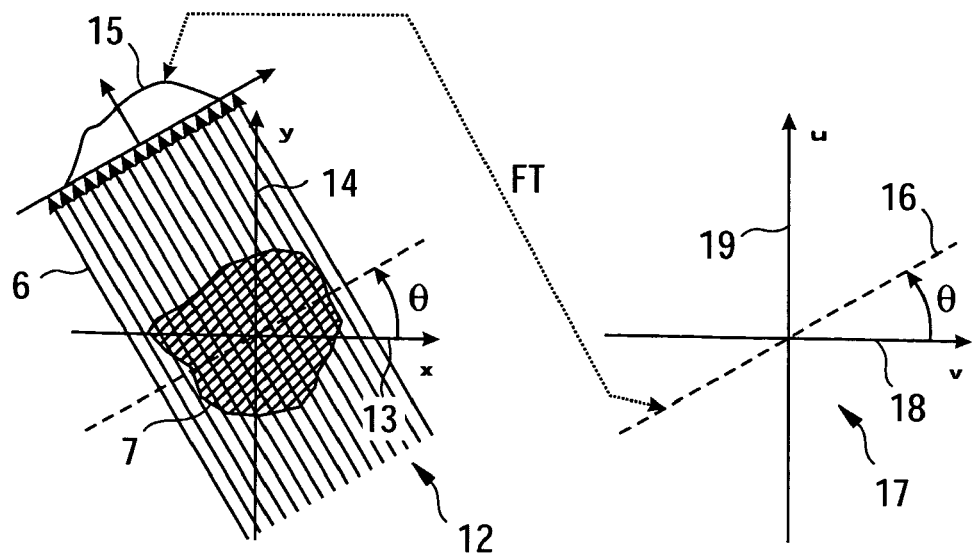
FIG. 2 shows a diagram illustrating the conversion of projection data to structural data.

For reconstruction of the structural data of the object 7, the Fourier Slice Theorem can be used because of the parallel beam geometry. FIG. 2 shows the object 7 which is transilluminated using the essentially parallel radiation bundles 6. The structure of the object 7 is described by a structure function which depends on spatial coordinates of a spatial coordinate system 12 with an x-axis 13 and a y-axis 14. Note that the rotation about the rotational axis 10 corresponds to rotation about a z-axis of the spatial coordinate system 12.

The projection data captured by the two-dimensional detector 12 is described by a projection function 15 which depends on two parameters s and t for a given rotation angle q. It can be shown that the Fourier transform of the projection function 15 yields the values of a two-dimensional Fourier transformation of the structure function describing the object in the projection plane along a plane 16 in the spatial frequency coordinate system 17. The spatial frequency coordinate system 17 is shown in FIG. 2 with the u-axis 19 and the v-axis 18. The third axis whose alignment corresponds to the alignment of the rotational axis has not been marked.

By capturing a plurality of projections with different angles θ, the values of the Fourier transforms of the structure function along a plurality of planes 16 passing through the origin of the spatial frequency coordinate system 17 at different angles θ can be determined. By means of an interpolation method, the values obtained can be transferred to a Cartesian coordinate system.

The reconstruction method for the structural data can be executed in two or three dimensions.

For execution in two dimensions, rows of detector sections 8 of the detector 9 are evaluated in each case. In accordance with the Fourier Slice Theorem, the structural data along adjacent cutting planes through the object 7 are reconstructed, the surface normal of these cutting planes running parallel to the rotational axis 10 in each case. The resolution along the rotational axis 10 is then determined by sampling.

The reconstruction method described with reference to FIG. 2 can also be extended to three dimensions. Thus the Fourier transform of a two-dimensional projected image yields the values of the Fourier transforms of the structure function along a plane passing through the origin of the spatial frequency coordinate system 17 and tilted by the angle θ. By re-interpolation and inverse Fourier transformation, the structure function in the spatial coordinate system 12 can then be obtained from the values in the spatial frequency coordinate system 17.

Because of the low beam divergence of the radiation bundles 6, the errors induced by the divergence of the radiation bundles 6 are negligible for the reconstruction of the object 7. In addition, the methods used for reconstructing the object 7 are relatively simple compared to a reconstruction method in which structural data is obtained from cone beam projection data.

Various possibilities exist for implementing the radiation source 4. The X-ray generator 2 can consist, for example, of a vacuum tube in which an electron beam scans a thin transmission target. The thermal load on the transmission target can be limited by liquid cooling.

For the collimator 3, a parallel hole collimator manufactured from an x-radiation absorbing material, in particular a material with a high atomic number Z, is especially suitable. Possible materials include Pb or W. The collimator 3 is preferably formed from a lead block containing a plurality of parallel holes.

In order to align the detector 9 to the collimator 3, the detector can perform a relative movement with respect to the radiation source 4. For example, it is possible to displace the detector relative to the radiation source 4 in a second cycle by dx, in the third cycle by dy and in the fourth cycle by dx+dy.

For the collimator 3, monochromators comprising e.g. a plurality of crystals or other monochromatizing elements such as multilayer structures can also be used. Capillary optics are also conceivable in order to increase the x-ray yields and therefore the x-ray intensity. Such x-ray optics are known to the person skilled in the art and as such are not the subject matter of the application.

In addition, the detector 3 can likewise be equipped with a collimator in order to suppress stray radiation.

It is to be expected that, by irradiating the entire volume in the object 7, the projection data required for reconstructing the structure of the object 7 can be obtained more quickly than in the prior art. Improved image quality is also to be expected, as the structure of the object 7 can be precisely reconstructed apart from the errors induced by the divergence of the radiation bundles 6. In addition, through the use of monochromatic radiation, the material, in particular its density and atomic number inside the object 7 can be reconstructed. The tomography equipment is therefore suitable, among other things, for material testing.

This computer tomography system according to the invention makes space- and time-resolving computer tomography using a large-area detector possible. Entire organs or regions of the body can thus be captured as volumes on a time-resolved basis. With a large-area detector of sufficiently high resolution, the computer tomography system can also be used to perform radiographic and fluoroscopic projection examinations.

The following emerge as direct advantages over computer tomography using fan beam geometry:
a) controllable primary profile in the beam volume.
b) homogeneous spectral source quality
c) simple beam geometry and therefore
d) simple and rapid reconstructions of the CT images.

The inventive step is the use of a plane parallel radiating large-area X-ray tube in combination with a large-area detector suitable for computer tomography.

The large-area X-ray tube and the large-area detector are diametrically mounted. During operation, the spatial cube between them is X-rayed on a plane parallel basis. The large-area detector measures the absorptions along parallel beam paths through the object under examination. The rest of the setup is of similar design to a conventional computer tomography system with rotating gantry.

This test arrangement has the following advantages:
a) The use of a controllable large-area X-ray tube with plane parallel radiation enables each detector pixel or detector section 8 to be assigned as little as one tube matrix element or emission section 5. The signal quality of each individual detector pixel can therefore be set during a dynamic computer tomography measurement. This feedback between the matrix control of the radiation source 4 and the large-area detector pixels is an important component of the computer tomography system according to the invention.
b) The beam geometry is plane parallel and therefore avoids anisotropic voxel sampling of the fan beam. Stray radiation can be more easily limited, as the alignment of the collimators to the focal point can now take place by means of exactly parallel arrangements.
c) Reconstruction is greatly simplified, as no further cone-beam corrections are necessary and simple back projection suffices instead.
d) The individual elements of the flat radiation source 4 can be operated without heel effect, as their individual solid emission angles are very small and in any case their operating principle need not be based on a rotating anode plate.

The term heel effect means that, in the X-ray tube, flat X-rays from the anode plate penetrate proportionately more anode material, causing them to be more heavily attenuated and hardened, resulting in a spectral composition dependent on the emission angle. This places certain requirements on the spectral linearity of the detector or requires spectral corrections in the reconstruction. At the same time the primary dose fluctuates over the fan beam and possibly therefore further increases the overall required dose.

Note that the tomography equipment 1 is primarily suitable for small animal imaging, as in this case only small volumes need to be irradiated with the radiation bundles 6 and only low radiation powers are required.

The invention claimed is:

1. A device for capturing structural data of an object, comprising:
   a radiation source comprising a plurality of adjacently disposed emission sections from which a respective plurality of radiation bundles are emitted substantially parallel with each other, the radiation source movable around the object along a trajectory;
   a detector disposed on an opposite side of the radiation source relative to the object and having movement in a manner similar to the movement of the radiation source, the detector having a plurality of adjacently disposed detector sections and generating projection data of the object;
   an evaluation unit adapted to compute the structural data of the object from the projection data captured by the detector,
   wherein each emission section applies the respective radiation bundle to a respective one of the detector sections, and
   wherein the evaluation unit is adapted to determine the structural data using a parallel beam algorithm.

2. The device according to claim 1, wherein the evaluation unit is adapted to determine the structural data on a volume basis by analyzing projection data of a plurality of the detector sections adjacently disposed in a plane.

3. The device according to claim 1, wherein the radiation source comprises an X-ray generator a first collimator disposed downstream in the beam path providing a collimated X-radiation bundle from each radiation section, more than 75% of which X-radiation bundle is incident on the respective detector section.

4. The device according to claim 3, wherein the collimator comprises a body made of X-ray-absorbing material with a plurality of adjacently disposed holes aligned in parallel, wherein more than 80% of each collimated X-radiation bundle is incident on the respective detector section.

5. The device according to claim 3, wherein a second collimator is disposed in front of the detector, wherein more than 95% of each collimated X-radiation bundle remaining after the second collimator is incident on the respective detector section.

6. The device according to claim 1, wherein the device is used for small animal imaging.

7. The device according to claim 1, wherein the device is used for nondestructive material testing.

8. The device according to claim 1, wherein the opposite side is a side of the object which is located opposite to that side of the object being exposed to radiation.

9. The device according to claim 1, when the detector moves such that the radiation source, the object and the detector are always arranged in line when operating the device.

10. The device according to claim 4, wherein the absorbing material is lead.

11. The device according to claim 4, wherein the absorbing material is wolfram.

12. The device according to claim 1, wherein the structural data are any of size, length, volume and geometry.

13. A device for capturing structural data of an object, comprising:
    a radiation source movable around the object along a trajectory;
    a detector disposed on an opposite side of the radiation source relative to the object and having movement in a manner similar to the movement of the radiation source, the detector having a plurality of adjacently disposed detector sections and generating projection data of the object; and an evaluation unit adapted to compute the structural data of the object from the projection data captured by the detector, wherein the radiation source has adjacently disposed emission sections, each emitting a substantially non-divergent radiation bundle to a respective detector section of the detector, each radiation bundle substantially parallel with others of the radiation bundles concurrently emitted;

wherein the evaluation unit is adapted to determine the structural data using a parallel beam algorithm, and wherein the evaluation unit is adapted to compute the structural data using a three-dimensional reconstruction method including Fourier transforms of a plurality of two-dimensional projected images recorded under a plurality of angles, each of the Fourier transforms of the plurality of two-dimensional projected images representing the Fourier transform of a structure function related to the object, the structure function evaluated along a plane passing through the origin of a spatial frequency coordinate system, the plane corresponding to a respective one of the plurality of angles.

14. A method of computing the structural data of claim 1 comprising using a two-dimensional reconstruction method including evaluating rows of the detector sections using the Fourier Slice Theorem such that the structure data along adjacent cutting planes through the objet are reconstructed, wherein the surface normal of each cutting plane runs parallel to a rotational axis related to the object.

* * * * *